United States Patent [19]

Baxendale

[11] 4,302,444
[45] Nov. 24, 1981

[54] VACCINES FOR IMMUNIZING EGG-LAYING BIRDS AGAINST EGG DROP DISEASE, PREPARATION OF SAID VACCINES, AND METHOD OF USE OF SAID VACCINES

[75] Inventor: William Baxendale, Houghton, Great Britain

[73] Assignee: Akzo N.V., Netherlands

[21] Appl. No.: 69,852

[22] Filed: Aug. 27, 1979

Related U.S. Application Data

[63] Continuation-in-part of Ser. No. 880,152, Feb. 22, 1978, abandoned.

[30] Foreign Application Priority Data

Mar. 4, 1977 [GB] United Kingdom ................ 9322/77

[51] Int. Cl.$^3$ .......................................... A61K 39/235
[52] U.S. Cl. ..................................... 424/89; 435/235; 435/236; 435/237; 435/238
[58] Field of Search ................... 424/89; 435/237–239

[56] References Cited

FOREIGN PATENT DOCUMENTS 2382500 9/1978 France .

OTHER PUBLICATIONS

Veterinary Bulletin 47 #1481, #6897 (1977) 48 #2966, #2971, #4417, #5414, #5417, #5421, #7257 (1978).
Vet. Bull. 49 #1309, #1317, #1318, #1319, #1916, #1967, #1969, #2516, #3925, #6605, #6607, #7287, #7285, #7297 (1979).
Vet. Bull. #6898 (1972) Stoenescu et al.
USPTO Translation Jun. 1980, Constantin and Hein "Prevention of the" 76 Egg-Laying Decline Syndrome by the Inactivated BC-14 Vaccine Strain AVi culteur 379:61–64 May 1978, French article.

*Primary Examiner*—Shep K. Rose
*Attorney, Agent, or Firm*—Stevens, Davis, Miller & Mosher

[57] ABSTRACT

There are disclosed novel vaccines for immunizing egg-laying birds against Egg Drop disease, a group of novel viruses (generically called EDS 76 virus) used in the preparation of such vaccines, and methods for immunizing egg-laying birds against Egg Drop disease or syndrome.

13 Claims, No Drawings

VACCINES FOR IMMUNIZING EGG-LAYING BIRDS AGAINST EGG DROP DISEASE, PREPARATION OF SAID VACCINES, AND METHOD OF USE OF SAID VACCINES

CROSS-REFERENCE TO RELATED APPLICATIONS

This application is a continuation-in-part of copending application Ser. No. 880,152 filed Feb. 22, 1978, now abandoned.

BACKGROUND OF THE INVENTION

The present invention relates to a process for the manufacture of vaccines for immunizing egg-laying birds, particularly chickens, against a disease (referred to herein as "Egg Drop disease") caused by a novel virus which adversely affects egg production and quality, to the vaccines so produced from the novel virus, and to the use of the vaccines.

Egg production is known to be adversely affected by a number of different factors, for example, poor food. A drop off in egg production sometimes is a side-effect of viral infections causing other diseases, e.g., those affecting the respiratory tract caused, for example, by an infection with Newcastle Disease Virus. An infection in chickens caused by Egg Drop disease virus was so far unknown or at least not widespread as appeared from the results of an examination of sera taken between 1973 and 1974 from 12 flocks which showed that none had antibodies to this virus. Recently, however, this particular type of Egg Drop disease has been observed in a number of countries. One of the features of this disease is that the shell gland may be affected, and egg production is depressed. Antibodies to this virus have been detected in 20 to 24 flocks of ducks sampled and the virus would appear to occur naturally in this species.

The casual organism of this disease appears to be a novel type of virus apparently unrelated to other known avian viruses, except insofar as certain minor proteins and morphological characteristics may be shared by avian adenoviruses.

SUMMARY OF THE INVENTION

I have now found the virus, generically called EDS 76 virus, which is responsible for Egg Drop disease. The invention relates in part to a group of novel viruses generically called EDS 76 virus encompassing a particularly isolated virus (virus EDS 76; VLO 100110/AV1 infra) and viruses antigenically related to the isolated virus that cross-react with the isolated virus both in the haemagglutination inhibition test and the neutralisation test.

The invention also relates to vaccines produced from this new virus type. The vaccines can be in an unattenuated form, an attenuated form, or an inactivated form.

The invention further includes methods of immunizing egg-laying birds against Egg Drop disease by administration of EDS 76 virus vaccines.

The virus can be isolated from buffy coat cells on chick embryo fibroblasts (CEF).[1] A culture medium of chick embryo fibroblasts was inoculated with this buffy coat and grown in a 5% $CO_2$-atmosphere at a temperature of 37.5° C. A cytophatic effect was observed after 2 to 4 days. The virus was found in both cells and tissue culture fluids.

[1]Buffy coat is the top layer of the sediment obtained after the centrifugation of blood.

The virus can also be isolated from other sources such as the oviducts and faeces of chickens, and from vent swabs taken from ducks.

The virus appears to be a heat-stable avian virus; in a wet state (i.e., in cell-culture fluids) the virus can survive for 6 days at room temperature with a fall in titer of less than 1 log.[10]. Other characteristics showing that EDS 76 virus is a new type of virus being unrelated to known avian viruses are the following:

Antisera produced by this virus do not cross neutralise with any of the known avian viruses.

The virus multiplies in the nucleus of the cells, and has poor growth in embryonated chicken eggs; both phenomena are characteristics of this virus.

The virus produces a cytopathic effect with plaque formation if cell cultures are overlayed with agar medium. Typical intranuclear eosinophilic inclusion bodies are produced in cell cultures.

Based on the results of the Virus Neutralisation Test (Plaque Reduction Test), and the Haemagglutination Inhibition Test, it has been shown also that the present virus is unrelated to other avian viruses. Moreover, the results obtained from the Gel Diffusion Test prove that this virus contains its own characteristic and distinct antigens.

The Haemagglutinin titre can be at least $10^5$ HA units/ml which means that chick erythrocytes are agglutinated even at a dilution of $10^5$ HA. This property differentiates this virus from a number of avian viruses, particularly currently known avian adenoviruses. The haemagglutinin referred to may consist of harvested supernatant from infected cultures and used in the test at room temperature without further treatment.

The virus grows on chick and duck cells such as kidney cells, embryo liver cells, and embryo fibroblasts. It also grows on embryonated duck eggs.

The above data sufficiently indentify this novel type of virus, and show that the virus is distinct from other avian viruses, e.g., Avian Influenza Viruses, Newcastle Disease Virus, Reovirus, Adenovirus, Leucosis Virus, Reticuloendotheliosis Virus, Avian Encephalomyelitis Virus, Herpes Virus including Infectious Laryngotracheitis, Marek's Disease Virus, Pigeon Herpes Viruses, Turkey Herpes Viruses, Infectious Bronchitis Virus, and Gumboro Disease Virus.

The novel virus (virus EDS 76) has been deposited at the Central Veterinary Laboratory, New Haw, Weybridge (number FLO 100110/AV1).

The instant invention is not restricted to virus EDS 76; as mentioned previously, the novel virus group of the present invention is distinct from other avian viruses but the virus here encompasses virus EDS 76 and its antigenically related viruses that cross-react with virus EDS 76 both in the haemagglutination inhibition test and the neutralization test. The group of EDS 76 viruses are antigenically related to one another but not related to known avian viruses.

The decrease of egg-laying in flocks infected with this type of virus is associated with an immune response; thus susceptible animals can be protected against this disease by vaccination.

As the virus causes no severe pathogenic effects in birds not in lay, the virus in its unattenuated form can be used for the production of a vaccine. It is also possible to produce a vaccine using a virus deprived of its infective properties without losing its antigenic activity, i.e., the ability to stimulate the production of antibodies. This may be effected by attenuation or by inactivation in which latter case the virus also loses its ability to multiply.

DESCRIPTION OF THE PREFERRED EMBODIMENTS

In accordance with the present invention, a vaccine is produced protecting against Egg Drop disease using the novel virus described above, and antigenically related viruses that cross-react in the haemagglutination inhibition test and the neutralization test in an either attenuated or unattenuated live form, or in an inactivated form.

The present invention also relates to such novel vaccines.

For the production of a live, unattenuated virus vaccine the virus is grown on cell tissue culture, preferably avian tissue culture (e.g., chick embryo fibroblast, embryo liver, or kidney cells) for 2 to 5 days, or in embryonated eggs. The tissue culture fluids and/or the cells are harvested, and in the case of embryonated eggs the embryos, and/or the membranes, and/or the allantoic fluids are harvested. Thereafter the preparation of a vaccine from the virus suspension is carried out in a manner known per se. It is advantageous to add a stabilizer, particularly if a dry preparation is prepared by lyophilization. An adjuvant such as aluminum hydroxide may also be added. The stabilizing agent can be a carbohydrate such as sorbitol, mannitol, starch, sucrose, dextran or glucose; a protein like albumin or casein; a protein-containing agent like bovine serum, or skimmed milk and a buffer such as an alkali metal phosphate. A preferred stabilizing agent is a mixture generally known as "SPGA" described by Bovarnick. (Journ. Bact. 59, 509 (1950)).

For the production of a live, attenuated virus vaccine, a number of methods are possible, e.g., adaptation of the isolated virus to a culture containing avian tissue cells, and attenuation, e.g., by 10 to 200 passages in such cultures, after which the virus is multiplied and a vaccine is prepared as given before for the production of a live, unattenuated virus vaccine.

Another method of producing live vaccine is to select and culture clones.

If the infected cells are used for the production of a live vaccine, it is advantageous to release the virus from the cells. This can be accomplished, e.g., by ultrasonic vibration.

Another possibility for producing a vaccine is to inactivate the virus. The inactivation can be carried out, e.g., with formaldehyde; with organic solvents, particularly halogenated hydrocarbons in the presence of a surface active agent, such as a polyoxyethylene sorbitan mono-oleate; or with β-propiolactone. This virus may also be inactivated by splitting the virus using one of a number of methods, e.g., by using an enzyme and/or an organic solvent. After inactivation, the pH may be adjusted to 7, the inactivating agent may be neutralized, e.g., formaldehyde is neutralized with thiosulphate, and the inactivated virus is mixed with an adjuvant. The adjuvant can be, for example, aluminum hydroxide, or a composition consisting of emulsifiers like Tween 80 and Span 80. (Marcol, Tween, and Span, are registered Trade Marks).

The vaccines, thus produced, either live or inactivated, will usually be given to birds at 10 to 20 weeks of age before coming into lay. With a live vaccine a dosage may be used in the range from $10^3$ to $10^8$ pfu per bird, but the vaccine should be given preferably at a dose of $10^5$ to $10^6$ pfu per bird. Administration can be by spray, drinking water, or injection. The inactivated vaccine must be injected. The minimum dose should be at least $10^2$ HA units per bird, and preferably greater than $4.10^2$ HA units per bird.

EXPERIMENTAL RESULTS

I. Safety Test

15×Specific pathogen free (SPF) day-old chickens infected intranasally with $10^7$ pfu/chick showed no clinical disease during a two-week observation period after inoculation.

II. Antibody Conversion and Safety Test

10×Nine week old SPF chickens given $10^7$ pfu developed specific haemagglutination inhibiting antibody and gel-precipitating antibody by 4 weeks post-inoculation. Again, no clinical disease was observed during a two-month period.

III. Pathogenicity Test in Laying Birds

18×SPF laying hens given $10^8$ pfu/chick intranasally showed a significant egg drop by 3-4 days post infection, whereas a control flock, not treated, did not show a drop.

IV. Protection Test of Inactivated Vaccine

Vaccine

Duck egg grown BC14 virus. BC14 virus is another name for virus EDS 76. Inactivated with 0.4% formalin and mixed with adjuvant:

| Water Phase | Oil Phase |
| --- | --- |
| Inactivated BC14 virus (800 HA units/dose) | Marcol 52 |
| Allantoic fluid | Tween 80 |
| Merthiolate (to 1/10,000) | Span 80 |
| Distilled Water | |

Experimental Design

Fifty broiler breeder hens and six cocks which were kept in isolation from hatching were divided into two even groups at 19 weeks of age. One group was vaccinated subcutaneously with the EDS vaccine and the other group left unvaccinated. The hens came into lay at 23 weeks and at 29 weeks; both groups were challenged by intraoccular instillation of one of our field isolates (strain M13) at a dose rate of $10^7$ pfu/bird.

Results

The unvaccinated group showed a marked drop in egg production (Table 1) after 6 days which persisted until 24 days. The hens also appeared sluggish and ate little from 5 to 7 days. The vaccinated birds were well protected against the effects caused by the challenge in the controls. Serological response 30 days post inoculation are shown in Table 2.

Conclusion

The vaccine provided excellent protection against the effects of a virulent strain of EDS virus.

TABLE 1

| Day | Number of Eggs | |
| --- | --- | --- |
| | Controls | Vaccinates |
| 1 | 16 | 16 |
| 2 | 14 | 16 |
| 3 | 14 | 17 |
| 4 | 14 | 15 |

TABLE 1-continued

| Day | Number of Eggs | |
|---|---|---|
| | Controls | Vaccinates |
| day of challenge | | |
| 5 | 13 | 15 |
| 6 | 14 | 14 |
| 7 | 14 | 14 |
| 8 | 14 | 14 |
| 9 | 13 | 15 |
| 10 | 5 | 15 |
| 11 | 5 | 13 |
| 12 | 2 | 13 |
| 13 | 2 | 13 |
| 14 | 3 | 13 |
| 15 | 3 | 14 |
| 16 | 2 | 14 |
| 17 | 2 | 15 |
| 18 | 2 | 15 |
| 19 | 2 | 15 |
| 20 | 3 | 15 |
| 21 | 3 | 15 |
| 22 | 3 | 18 |
| 23 | 3 | 18 |
| 24 | 5 | 17 |
| 25 | 5 | 17 |
| 26 | 5 | 17 |
| 27 | 5 | 16 |
| 28 | 6 | 16 |

TABLE 2

Response of 19 week old broiler breeders to BC14 inactivated vaccine (30 days post-inoculation).

| Vaccinated Group | Antibody Titres | | |
|---|---|---|---|
| | HI | Neutralisation Test | Gel Diffusion |
| 1 | 64 | 2048 | + |
| 2 | 128 | 2048 | + |
| 3 | 64 | 2048 | + |
| 4 | <8 | 32 | − |
| 5 | 128 | 2048 | + |
| 6 | 64 | 2048 | + |
| 7 | 128 | 2048 | + |
| 8 | 64 | 2048 | + |
| Control Group 10 | All <8 | All <16 | All − |

The following Examples illustrate the invention.

EXAMPLE 1

Isolation of Virus

20 Blood samples were taken from randomly selected birds from one flock. The white blood cells were separated from the samples after centrifugation and 0.2 ml of packed cells were inoculated onto each of two CEF cell culture plates (6 cms.).

After 24 hours incubation in 5% $CO_2$ atmosphere at 37° C., the white cells were poured off in the supernatant fluid, the cultures washed in phosphate buffered saline 1 (PBS), and the medium replenished. After a further 72 hours incubation a cytopathic effect was observed in cell cultures inoculated with two of the blood samples.

Additionally, haemagglutinins were found in the supernatants of the four positive plates.

EXAMPLE 2

Preparation of Inactivated Vaccine

Antigen Preparation

Chick embryo liver cell cultures were prepared from 14 days incubated SPF embryonated eggs by removing the livers from the embryos, washing in PBS, and then trypsinising using a 0.25% Trypsin solution in PBS at 37° C. The cells were deposited by centrifugation, the supernatant discarded, and the cells resuspended in growth medium. The content of the growth medium is as follows:

| | | |
|---|---|---|
| Eagles Minimim Essential Medium | | 80 parts |
| Tryptose Phosphate Broth (30 gms/l) | | 10 parts |
| 2.5% Aqueous Sodium Bicarbonate | | 4 parts |
| Bovine Calf Serum | | 15 parts |
| Penicillin (100 units/ml) | } | |
| Streptomycine (0.1 mg/ml) | | 6 parts |
| Mycostatin (25 units/ml) | | |

Plates were then seeded at the rate of $3 \times 10^6$ cells in 5 ml per 6 cm plate or $40 \times 10^6$ cells in 20 ml per 15 cm plate.

After 24 hours incubation at 37° C. in $5CO_2$ atmosphere, the cell cultures were inoculated with the EDS virus at approximately $10^6$ pfu per 6 cm or $10^7$ pfu per 15 cm plate. The cultures were then incubated for a further 72 hours.

The supernatant fluids were harvested and the infected cells removed from the plates by a rubber policeman. The cells were then pooled with the supernatant fluid and the whole frozen down to −70° C.

The pool was thawed after storage and diluted ten-fold with distilled water.

Inactivation

A cold solution of β-propiolactone was added to the thawed pool to give a final concentration of 0.2%. After 2 hours incubation at 37° C., the pH of the solution was adjusted to pH 7.0 with N/1 sodium hydroxide solution. The preparation when inoculated onto cell cultures failed to induce a cytopathic effect.

Adjuvant Addition

| Composition: | MARCOL 32 | 90% |
|---|---|---|
| | TWEEN 80 | 3.5% |
| | SPAN 80 | 6.5% |

The antigen is titrated by the haemagglutination test using chicken erythrocytes and the volume adjusted with water for injection so that when mixed with an equal volume of adjuvant the final emulsion will contain 400 HA units per bird dose (0.5 ml can be used as a bird dose). The mixture is then passed through an emulsifier.

EXAMPLE 3

Live Vaccine (attenuated or unattenuated)

The antigen was prepared as described in Example 2 up to the stage of freezing down to −70° C. using a designated strain of vaccine virus (attenuated or unattenuated).

After thawing, the pool was diluted with an equal volume of SPGA stabilizer, filled into vials in 2 ml quantities and lyophilized.

Subsequently, samples were titrated and shown to contain live virus at high titre.

What is claimed is:

1. A process for the preparation of a live, unattenuated vaccine that protects egg-laying birds against the Egg Drop disease comprising growing an EDS 76 virus selected from the group consisting of virus EDS 76 (VLO 10110/AV1) on cell tissue culture and harvesting the infected culture material selected from the group consisting of tissue culture fluids, the cells, and mixtures thereof.

2. A process for the preparation of a live, unattenuated vaccine that protects egg-laying birds against the Egg Drop disease comprising growing an EDS 76 virus selected from the group consisting of virus EDS 76 (VLO 10110/AV1) in embryonated eggs and harvesting any of the embryos, the membranes, and allantoic fluids.

3. A process for the preparation of a live, attenuated vaccine that protects egg-laying birds against the Egg Drop disease comprising adapting an EDS 76 virus selected from the group consisting of virus EDS 76 (VLO 10110/AV1) to an avian tissue cell-containing culture and undertaking a plurality of passages of said virus in said culture to multiply said virus.

4. A process for the preparation of an inactivated vaccine that protects egg-laying birds against the Egg Drop disease comprising inactivating an EDS 76 virus selected from the group consisting of virus EDS 76 (VLO 10110/AV1) with an inactivating agent selected from the group consisting of an enzyme, an organic solvent, formaldehyde, $\beta$-propiolactone, and mixtures of an enzyme and an organic solvent.

5. The process of claim 4 wherein said organic solvent is an halogenated hydrocarbon.

6. The process of claim 4 wherein said inactivating agent is formaldehyde.

7. The process of claim 4 wherein said inactivating agent is $\beta$-propiolactone.

8. A vaccine effective against Egg Drop disease comprising an EDS 76 virus selected from the group consisting of virus EDS 76 (VLO 10110/AV1) in an unattenuated form.

9. A vaccine effective against Egg Drop disease comprising an EDS 76 virus selected from the group consisting of virus EDS 76 (VLO 10110/AV1) in an attenuated form.

10. A vaccine effective against Egg Drop disease comprising an EDS 76 virus selected from the group consisting of virus EDS 76 (VLO 10110/AV1) in an inactivated form.

11. A method of immunizing egg-laying birds against Egg Drop disease comprising administering to egg-laying birds the vaccine of claims 8 to 10.

12. The method of claim 11 comprising administering a live vaccine in a dosage ranging from $10^3$ to $10^8$ pfu per bird.

13. The method of claim 11 comprising administering an inactivated vaccine in a dosage of at least $10^2$ HA units per bird.

* * * * *